United States Patent [19]
Afzal

[11] Patent Number: 6,083,198
[45] Date of Patent: Jul. 4, 2000

[54] PERFUSION CATHETER PROVIDING SEGMENTED FLOW REGIONS AND METHODS OF USE

[75] Inventor: Thomas A. Afzal, Menlo Park, Calif.

[73] Assignee: Cardiovention, Inc., Palo Alto, Calif.

[21] Appl. No.: 09/104,961

[22] Filed: Jun. 25, 1998

[51] Int. Cl.[7] .................................................. A61M 29/00
[52] U.S. Cl. .............................. 604/101.01; 604/101.03; 604/102.01
[58] Field of Search ................................... 604/4, 5, 6, 8, 604/96, 101, 102, 528, 101.01, 101.03, 101.05, 102.01; 606/192, 194

[56] References Cited

U.S. PATENT DOCUMENTS

| | | |
|---|---|---|
| 4,173,981 | 11/1979 | Mortensen . |
| 4,705,507 | 11/1987 | Boyles . |
| 4,943,275 | 7/1990 | Stricker . |
| 5,116,305 | 5/1992 | Milder et al. . |
| 5,158,540 | 10/1992 | Wijay et al. .......................... 604/102 X |
| 5,312,344 | 5/1994 | Grinfeld et al. . |
| 5,433,700 | 7/1995 | Peters . |
| 5,484,412 | 1/1996 | Pierpont .............................. 604/102 X |
| 5,584,803 | 12/1996 | Stevens et al. . |
| 5,735,290 | 4/1998 | Sterman et al. . |
| 5,810,757 | 9/1998 | Sweezer, Jr. et al. .............. 604/102 X |

*Primary Examiner*—Wynn Wood Coggins
*Assistant Examiner*—A. T. Nguyen
*Attorney, Agent, or Firm*—Fish & Neave; Nicola A. Pisano

[57] ABSTRACT

Apparatus and methods are provided for delivering oxygenated blood at a first flow rate to a first region of the body and at a second lower flow rate to a second region of the body using first and second balloons and a first lumen that delivers blood to a first plurality of apertures interposed between the first and second balloons. A second lumen is used to deliver blood to a second plurality of apertures disposed proximally of the second balloon. Methods of using the apparatus also are provided.

11 Claims, 3 Drawing Sheets

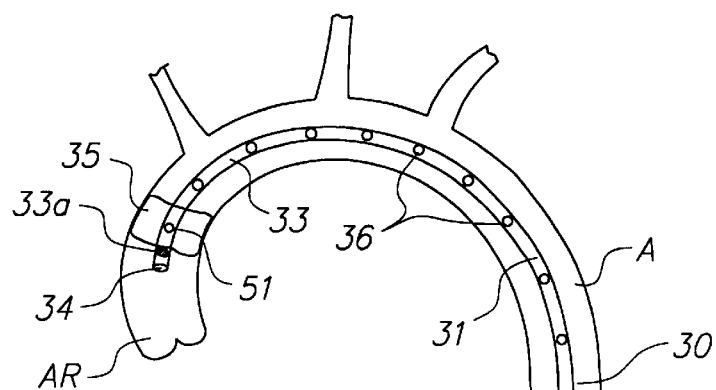
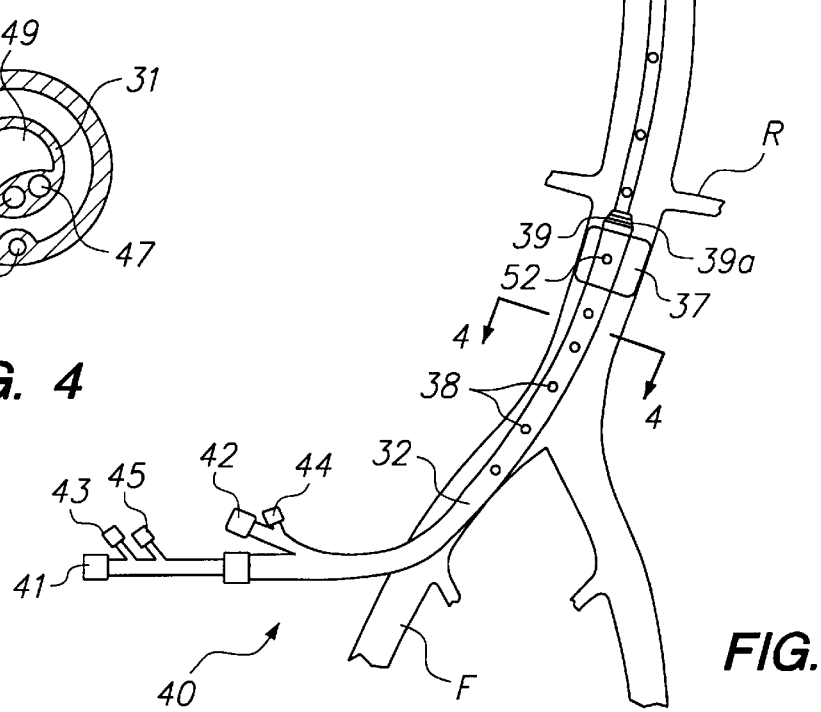
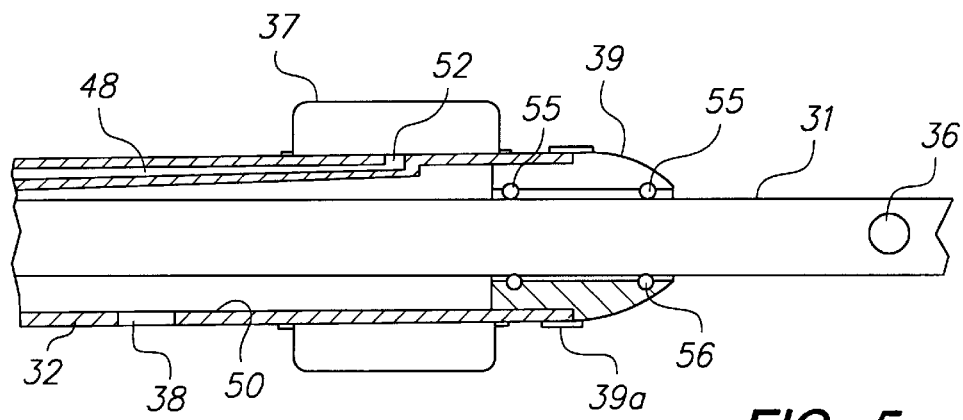
FIG. 4
FIG. 3
FIG. 5

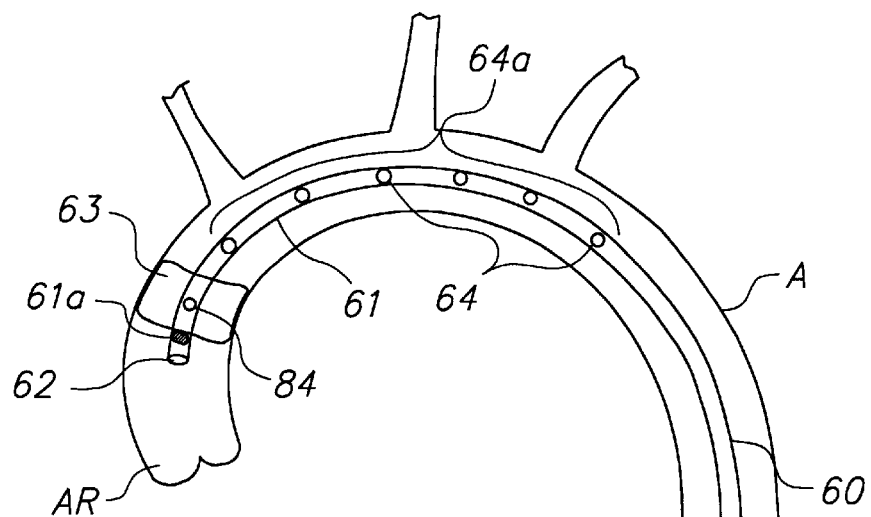
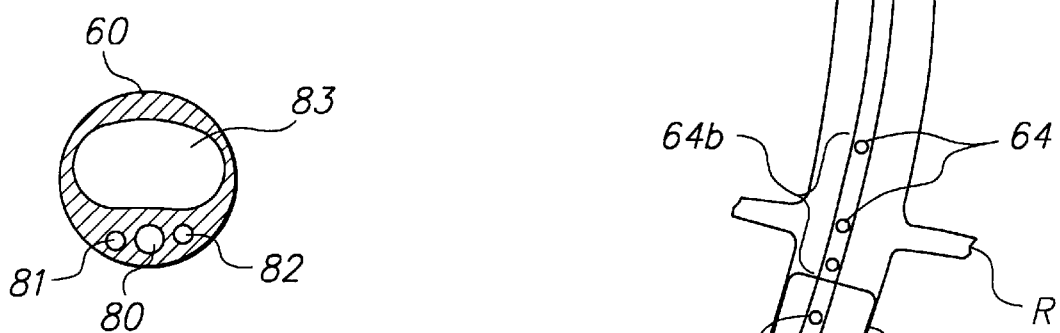
FIG. 7
FIG. 6

PERFUSION CATHETER PROVIDING SEGMENTED FLOW REGIONS AND METHODS OF USE

FIELD OF THE INVENTION

The present invention relates to catheters used to return oxygenated blood from a cardiopulmonary bypass machine to a patient during cardiac surgery. More specifically, the present invention relates to a perfusion catheter, and methods of use, that provide different flow rates to different regions of the body.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

More recently, techniques are being developed, for example, by Heartport, Inc., Redwood City, Calif., that permit cardiac surgery using an endoscopic approach, in which small access openings are created between the ribs and the bypass graft or heart valve repair procedure is performed guided by an image displayed on a video monitor. In the "keyhole" techniques developed by Heartport, the patient's heart is stopped and the patient is placed on cardiopulmonary bypass. Still other techniques being developed, for example, by CardioThoracic Systems, Inc., of Cupertino, Calif., enable such bypass graft procedures to be performed on a beating heart.

In those techniques that involve stopping the heart to perform the surgery, blood flow to the heart is occluded, for example, by placing occlusion balloons in the ascending aorta and/or the vena cava. Venous blood is then withdrawn from the patient, for example, from the vena cava, and oxygenated using an extracorporeal oxygenation circuit. The oxygenated blood is then perfused into the patient in the vicinity of the ascending aorta to provide oxygenated blood to the brain, internal organs and extremities.

U.S. Pat. No. 5,312,344 to Grinfeld et al. describes a multi-lumen perfusion catheter for perfusing oxygenated blood into a patient on cardiopulmonary bypass. The catheter has a distal balloon for occluding the ascending aorta, a first lumen for delivering cardioplegia solution through a first opening distal to the balloon, and a second lumen for perfusing oxygenated blood through a second opening proximal to the balloon. The catheter may be positioned in the ascending aorta either directly through an opening in the aorta, or in a retrograde manner via a femoral artery and the abdominal aorta.

U.S. Pat. No. 4,173,981 to Mortensen describes an arterial perfusion catheter having a tapered shape and a plurality of openings along its length. When the catheter is positioned within a patient, one or more openings preferably are aligned with the branch vessels in the aortic arch, the renal arteries, the iliac bifurcation, and the internal iliac artery.

The foregoing catheters have a number of disadvantages. In particular, multi-lumen catheters, such as described in Grinfeld et al., must have a large diameter to provide oxygenated blood sufficient to perfuse the whole body. In addition, because the foregoing catheters preferably are positioned with the blood perfusion openings in predetermined locations, a variety of catheters of different lengths must be available for use in patients of different sizes.

The perfusion system described in the literature by Heartport, Inc., Redwood City, Calif., comprises an "endo-aortic clamp" ("EAC") portion and an arterial return catheter ("ARC"). The EAC, which comprises a catheter having a balloon for occluding the aortic root, and a lumen for delivering cardioplegia distal to the balloon, passes through the ARC. The ARC extends only a short distance into the patient's femoral artery. Oxygenated blood is perfused through the annulus formed by the ARC and the EAC and in a retrograde manner in the aorta.

A drawback associated with all of the foregoing perfusion systems is that all require relatively high performance pumps to deliver flow rates high enough to perfuse the entire body. In multi-lumen catheter designs, the pressure drop encountered in delivering a high flow rate proximal to the occlusion balloon favors the use of larger diameter lumens, thereby resulting in catheters having a profile too large to fit many patients having smaller frames or vessels.

Similarly, in the Heartport system, the need to perfuse the blood in a retrograde fashion along the length of the aorta requires a high performance pump. This is especially so because the oxygenated blood is perfused into the iliac artery, where the degree of oxygenation is relatively low, and must then flow in a retrograde manner through the aorta to reach the aortic arch, where the highest flow rates are required to preserve the brain.

In view of the foregoing, it would be desirable to provide apparatus and methods for delivering oxygenated blood to a patient from a cardiopulmonary bypass machine, and that overcome the drawbacks of previously known perfusion catheters.

It further would be desirable to provide apparatus and methods for delivering oxygenated blood to a patient that permit the use of one or more lower performance pumps than has heretofore been possible.

It still further would be desirable to provide apparatus and methods for delivering flow rates to different regions of the body in proportion to the degree of oxygenation required by those different regions.

SUMMARY OF THE INVENTION

In view of the foregoing, it is an object of this invention to provide apparatus and methods for delivering oxygenated blood to a patient from a cardiopulmonary bypass machine, and that overcome the drawbacks of previously known perfusion catheters.

It is a further object of the present invention to provide apparatus and methods for delivering oxygenated blood to a patient that permit the use of one or more lower performance pumps than has heretofore been possible.

It is another object of this invention to provide apparatus and methods for delivering flow rates to different regions of the body in proportion to the degree of oxygenation required by those different regions.

These and other objects of the invention are accomplished by providing a perfusion catheter having a first and second balloons, a first lumen capable of delivering oxygenated blood to a first plurality of apertures interposed between the first and second balloons, and a second lumen capable of delivering blood to a second plurality of apertures disposed proximally of the second balloon. In accordance with the principles of the present invention, the perfusion catheter delivers oxygenated blood at a first flow rate to the region between the first and second balloons, and delivers oxygenated blood at a second flow rate to the region proximal of the second balloon.

In one embodiment, the perfusion catheter includes a first inlet port communicating with the first lumen, and a second inlet port communicating with the second lumen. The first and second lumens may be sized so that, when coupled to an outlet of a single cardiopulmonary bypass machine, the flow rates exiting the first and second pluralities of apertures are adequate to provide whole body perfusion. The first and second balloons and first and second lumens may be integral in a single multi-lumen catheter.

Alternatively, the first balloon and first lumen may form part of a first catheter and the second balloon and second lumen may form part of a second catheter that is longitudinally adjustable relative to the first catheter. The first catheter delivers oxygenated blood at a first flow rate to a first region of the body defined by placement of the first and second balloons, while the second catheter delivers oxygenated blood at a second flow rate to a second region of the body.

As further alternative, the first and second balloons, and first lumen may form part of a first catheter that is inserted via a first access site to perfuse a first region of the body while the second lumen may form part of a second catheter that is inserted via a second access site to perfuse a second region of the body.

BRIEF DESCRIPTION OF THE DRAWINGS

Further features of the invention, its nature and various advantages will be more apparent from the accompanying drawings and the following detailed description of the preferred embodiments, in which:

FIG. 3 is a side view of an alternative embodiment of a perfusion catheter constructed in accordance with the present invention;

FIG. 4 is a cross-sectional view of the perfusion catheter of FIG. 3 taken along view line 4—4 of FIG. 3;

FIG. 5 is a side-sectional view of the perfusion catheter of FIG. 3 in the region of the proximal balloon;

FIG. 6 is a side view of another alternative embodiment of a perfusion catheter constructed in accordance with the present invention; and FIG. 7 is a cross-sectional view of the perfusion catheter of FIG. 6 taken along view line 7—7 of FIG. 6.

DETAILED DESCRIPTION OF THE INVENTION

Figures 1, 2:
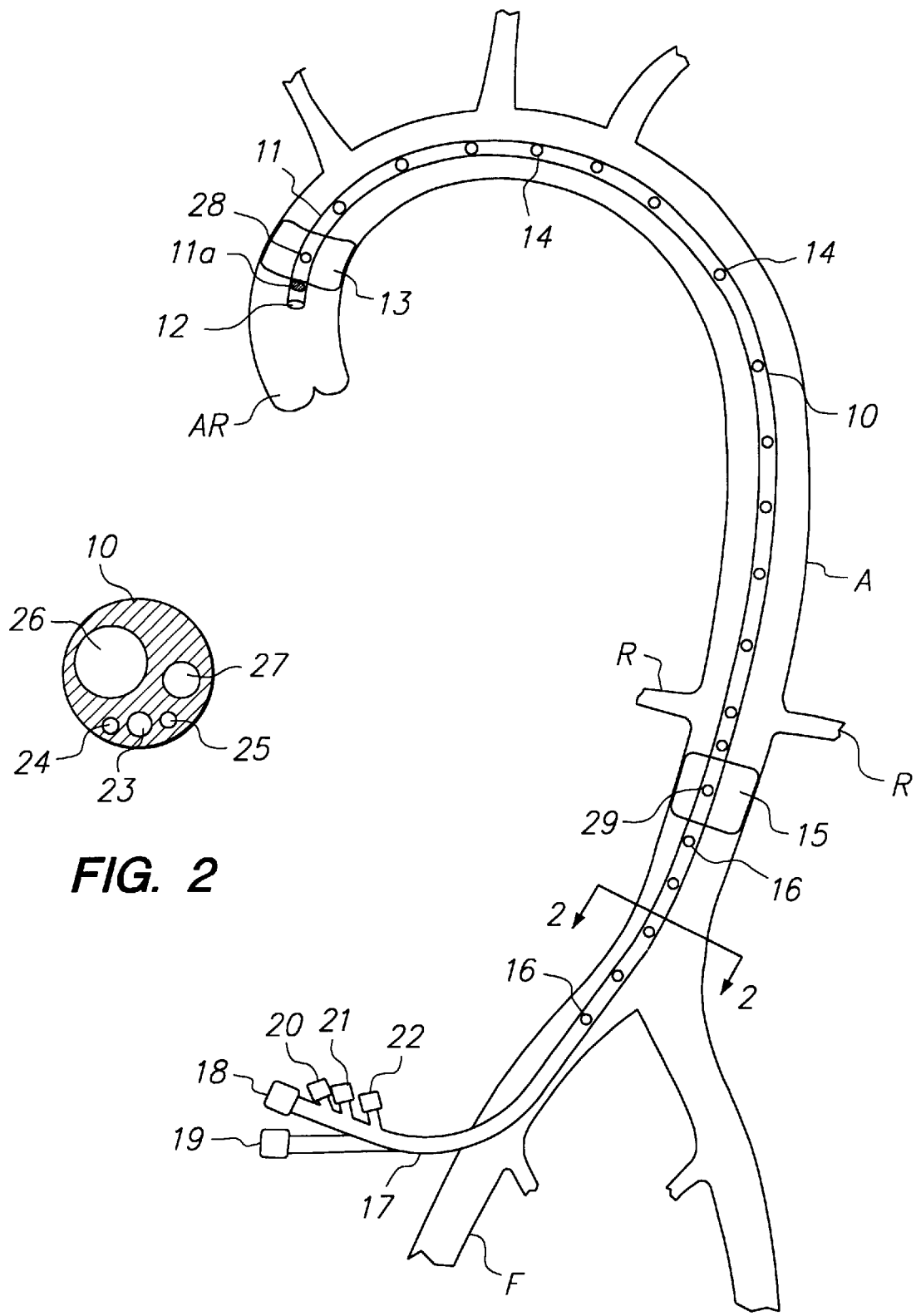
FIG. 1 is a side view of an illustrative embodiment of a perfusion catheter constructed in accordance with the present invention.
FIG. 2 is a cross-sectional view of the perfusion catheter of FIG. 1 taken along view line 2—2 of FIG. 1.

The present invention provides a perfusion catheter that provides different flow rates of oxygenated blood to different regions of a patient's body. Perfusion catheters constructed in accordance with the principles of the present invention are based on the observation that, during cardiac surgery, some regions of the body, such as the brain, require near-normal blood flow rates to avoid injury, while other regions of the body, such as the lower extremities, can tolerate much lower blood flow rates without injury. It is expected that the perfusion catheters of the present invention may reduce the need for high performance pumps by reducing the overall volume of blood that must be perfused into the body by up to 40%.

Specifically, the perfusion catheters of the present invention enable smaller, lower performance pumps to be used to provide high flow rates, but at reduced volumes, to critical areas of the body, such as the branch vessels of the aortic arch. A second lumen is provided for delivering oxygenated blood to the remainder of the body, but at much lower flow rates. Unlike the multi-lumen catheter described in the Grinfeld et al. patent, the catheters of the present invention do not attempt to provide whole-body perfusion. Accordingly, the portion of the catheter that extends into the aortic arch may be much smaller in diameter. Moreover, because the remainder of the body is perfused at a lower flow rate, a smaller diameter lumen also may be used.

Referring to FIG. 1, an illustrative perfusion catheter constructed in accordance with the principles of the present invention is described. Catheter 10 comprises distal end 11 having radioopaque marker band 11a, outlet port 12, distal balloon 13, apertures 14, proximal balloon 15 and apertures 16. Proximal end 17 of catheter 10 includes blood inlet ports 18 and 19, balloon inflation ports 20 and 21, and cardioplegia injection port 22. Catheter 10 is shown positioned within aorta A with distal balloon 13 positioned near aortic root AR, proximal balloon 15 positioned just below renal arteries R, and the proximal portion of the catheter exiting through a cut-down in femoral artery F.

Referring now also to FIG. 2, lumen 23 couples cardioplegia injection port 22 to outlet port 12. Lumen 24 couples balloon inflation port 20 to distal balloon 13, while lumen 25 couples balloon inflation port 21 to proximal balloon 15. Lumen 26 couples blood inlet port 18 to apertures 14, while lumen 27 couples blood inlet port 19 to apertures 16.

Cardioplegia solution injected into cardioplegia injection port 22 exits catheter 10 through outlet port 12. Oxygenated blood pumped into catheter 10 via blood inlet port 18 exits the catheter only through apertures 14, while blood pumped into catheter 10 via blood inlet port 19 exits the catheter only through apertures 16. One or more apertures 28 communicate inflation medium injected via balloon inflation port 20 and lumen 24 with the interior of balloon 13. Likewise, one or more apertures 29 communicate inflation medium injected via balloon inflation port 21 and lumen 25 with the interior of balloon 15.

Catheter 10 may be constructed of any of a number of materials commonly used in catheter construction, such as polyethylene, polyurethane, or polyvinylchloride. Distal balloon 13 and proximal balloon 15 may comprise a non-compliant or semi-compliant material, such as polyethylene, polyurethane, or nylon. Inlet ports 18–22 are equipped with standard luer connections that permit coupling to a source of inflation medium, cardioplegia solution, and a cardiopulmonary bypass machine, respectively.

In accordance with the principles of the present invention, catheter 10 may be coupled to a cardiopulmonary bypass machine so that blood may be pumped through apertures 14 in the region of the aorta between balloons 13 and 15 at a flow rate of up to 7–8 liters/minute, and blood may be pumped through apertures 16 at flow rates of up to 3–4 liters/minute. Blood inlet ports 18 and 19 therefore may be coupled to two separate pumps, or coupled to a Y-shaped connector (not shown) on the outlet of a single pump. In the latter case, the diameters of lumens 26 and 27 may be selected to provide the desired flow rates.

In operation, catheter 10 first is positioned in a patient's aorta via a femoral cut-down, and then advanced so that distal end 11 is positioned in the ascending aorta, for example, as determined by fluoroscopy and suitable radioopaque marker 11a. Once the catheter is in place and connected to a cardiopulmonary bypass machine, distal balloon 13 is inflated. Cardioplegia solution then is injected via port 22, lumen 23 and outlet port 12 to stop the heart. Proximal balloon 15 is inflated, and the cardiopulmonary bypass machine may then be activated to perfuse the upper and lower regions of the body at different flow rates.

Advantageously, because the total volumetric flow rate required to perfuse the body using catheter 10 is expected to be significantly lower than previously known perfusion arrangements, lower performance, less costly pumps may be used. This in turn may contribute to an overall reduction in the cost of the bypass procedure.

Referring now to FIG. 3, an alternative embodiment of a perfusion catheter constructed in accordance with the present invention is described. Catheter 30 comprises inner catheter 31 disposed for sliding movement in outer catheter 32. Inner catheter 31 comprises distal end 33 having radioopaque marker band 33a, outlet port 34, distal balloon 35 and apertures 36. Outer catheter 32 comprises proximal balloon 37, apertures 38 and endcap 39 including radioopaque marker band 39a. Proximal end 40 of catheter 30 includes blood inlet ports 41 and 42, balloon inflation ports 43 and 44, and cardioplegia injection port 45. Catheter 30 is shown positioned within aorta A with distal balloon 35 positioned near aortic root AR, proximal balloon 37 positioned just below renal arteries R, and the proximal portion of the catheter exiting through a cut-down in femoral artery F.

Referring now also to FIG. 4, lumen 46 couples cardioplegia injection port 45 to outlet port 34. Lumen 47 couples balloon inflation port 43 to distal balloon 35, while lumen 48 couples balloon inflation port 44 to proximal balloon 37. Lumen 49 couples blood inlet port 41 to apertures 36. Annulus 50, defined by the exterior of inner catheter 31 and the interior surface of catheter 32 forms a lumen that couples blood inlet port 42 to apertures 38.

Cardioplegia solution injected into cardioplegia injection port 45 exits inner catheter 31 through outlet port 34. Oxygenated blood pumped into inner catheter 31 via blood inlet port 41 exits the catheter only through apertures 36, while blood pumped into catheter 30 via blood inlet port 42 exits the outer catheter 32 only through apertures 38. One or more apertures 51 communicate inflation medium injected via balloon inflation port 43 and lumen 47 with the interior of distal balloon 35. Likewise, one or more apertures 52 communicate inflation medium injected via balloon inflation port 44 and lumen 48 with the interior of proximal balloon 37.

As shown in FIG. 5, inner catheter 31 preferably is disposed concentrically in outer catheter 32 for sliding movement by O-rings 55 disposed in recesses 56 of endcap 39. Accordingly, the longitudinal spacing between distal balloon 35 and proximal balloon 37 may be adjusted by sliding inner catheter 31 relative to outer catheter 32. Consequently, catheter 30 may be used for a variety of patients of different size, with the spacing between the distal and proximal balloons adjusted on a per-patient basis. Radioopaque markers 33a and 39a assist in visualizing this positioning of the catheter under fluoroscopic guidance.

Catheters 31 and 32, and endcap 39, may be constructed of any of the materials described hereinabove, such as polyethylene, polyurethane, or polyvinylchloride, while balloons 35 and 37 likewise may comprise a noncompliant or semi-compliant material, as described above. O-rings 55 preferably comprise a biocompatible material, such as silicone or polytetrafluoroethylene. Inlet ports 41–45 preferably are equipped with standard luer connections, as described hereinabove.

Catheter 30 may be coupled to a single or multiple pumps, as described hereinabove. If catheter 30 is to be designed so that blood inlet ports 41 and 42 are to be coupled to a single pump using a Y-connection, the diameters of lumens 49 and 50 may be selected to control the flow rates delivered through apertures 36 and 38.

Operation of catheter 30 is similar to that described hereinabove with respect to catheter 10. In particular, catheter 30 first is positioned in a patient's aorta via a femoral cut-down, and then advanced so that distal end 33 is positioned in the ascending aorta, for example, as determined by fluoroscopy and radioopaque marker 33a. Outer catheter 32 is then adjusted in the proximal and distal directions until proximal balloon 37 is disposed in a desired position, e.g., either above or below renal arteries R, as determined by fluoroscopy and radioopaque marker 39a.

Once catheter 30 is in place and connected to a cardiopulmonary bypass machine, distal balloon 35 is inflated. Cardioplegia solution then is injected via port 45, lumen 46 and outlet port 34 to stop the heart. Proximal balloon 37 is inflated, and the cardiopulmonary bypass machine may then be activated to perfuse the upper and lower regions of the body at different flow rates. Catheter 30 provides not only the advantages of catheter 10, described hereinabove, but also permits the catheter to be employed in patients of different sizes by adjusting the spacing the distal and proximal balloons.

With respect to FIG. 6, a further alternative embodiment of a perfusion catheter of the present invention, suitable for very small frame patients, is described. Catheter 60 comprises distal end 61 having radioopaque marker band 61a, outlet port 62, distal balloon 63, apertures 64, and proximal balloon 65. Proximal end 66 of catheter 60 includes blood inlet port 67, balloon inflation ports 68 and 69, and cardioplegia injection port 70. Catheter 60 is used in conjunction with return catheter 75. Return catheter 75 comprises a single lumen catheter having distal end 76 including radioopaque marker band 76a, plurality of apertures 77 and proximal end 78 including luer fitting 79 for connecting the catheter to a cardiopulmonary bypass machine.

Catheter 60 is shown in FIG. 6 positioned within aorta A with distal balloon 63 positioned near aortic root AR, proximal balloon 65 positioned just below renal arteries R, and the proximal portion of the catheter exiting through a cut-down in femoral artery $F_1$. Return catheter 75 is positioned in aorta A with distal end 76 disposed above iliac bifurcation IB, and exits through a cut-down in femoral artery $F_2$.

Referring now also to FIG. 7, lumen 80 couples cardioplegia injection port 70 to outlet port 62. Lumen 81 couples balloon inflation port 68 to distal balloon 63, while lumen 82 couples balloon inflation port 69 to proximal balloon 65. Lumen 83 couples blood inlet port 67 to apertures 64. Apertures 64 preferably are arranged in two groups along the length of catheter 60, so that first group 64a is disposed in the aortic arch and second group 64b is disposed adjacent renal arteries R.

Cardioplegia solution injected into cardioplegia injection port 70 exits catheter 60 through outlet port 62. Oxygenated blood pumped into catheter 60 via blood inlet port 67 exits the catheter only through apertures 64. One or more apertures 84 communicate inflation medium injected via balloon inflation port 68 and lumen 81 with the interior of distal balloon 63. Likewise, one or more apertures 85 communicate inflation medium injected via balloon inflation port 69 and lumen 82 with the interior of proximal balloon 65.

Catheters 60 and 75, and balloons 63 and 65 may be constructed of any of the materials described hereinabove. Inlet ports 67–70 and 79 preferably are equipped with standard luer connections, as described hereinabove. Radioopaque markers 61a and 76a assist in positioning the catheters under fluoroscopic guidance.

Use of catheters 60 and 75 is now described. Catheter 60 first is positioned in a patient's aorta via a femoral cut-down in femoral artery $F_1$, and then advanced so that distal end 61 is positioned in the ascending aorta, for example, as determined by fluoroscopy and radioopaque marker 61a. Return catheter 75 is positioned in the patient's aorta, below the position of balloon 65 and above iliac bifurcation IB, via a femoral cut-down in femoral artery $F_2$, as determined by fluoroscopy and radioopaque marker 76a.

Once catheters 60 and 75 are in place and connected to a cardiopulmonary bypass machine, distal balloon 63 is inflated to occlude the aorta. Cardioplegia solution then is injected via port 70, lumen 80 and outlet port 62 to stop the heart. Proximal balloon 65 is inflated, and the cardiopulmonary bypass machine then may be activated to perfuse the upper region of the body at a first flow rate via blood inlet port 67, lumen 83, and apertures 64. Catheter 75 is used to perfuse the lower region of the body at a second, lower, flow rate. Catheters 60 and 75 therefore provide many of the advantages of catheters 10 and 30, described hereinabove, but also permit the catheter system to be employed in patients of very small size or having very small femoral arteries.

While preferred illustrative embodiments of the invention are described above, it will be apparent to one skilled in the art that various changes and modifications may be made therein without departing from the invention. For example, the various lumens depicted in the illustrative cross-sections of FIGS. 2, 4, 5 and 7 may have alternative arrangements, and it is intended in the appended claims to cover all such changes and modifications which fall within the true spirit and scope of the invention.

What is claimed is:

1. A catheter for use in cardiopulmonary bypass and adapted to deliver blood at a first flow rate in a first region of a patient's aorta including the aortic arch and renal arteries, and to deliver blood at a second flow rate in a second region of the patient's aorta distal to the renal arteries, the catheter comprising:

a catheter having proximal and distal ends, first and second lumens, and first and second blood inlet ports, the first lumen communicating with the first blood inlet port and the second lumen communicating with the second blood inlet port;

a first balloon disposed on the catheter adjacent the distal end;

a second balloon disposed on the catheter spaced apart from the first balloon a sufficient distance so that when the first balloon is disposed in the patient's ascending aorta the second balloon is disposed in the patient's aorta distal to the renal arteries;

a first plurality of apertures disposed in the catheter between first and second balloons and in communication with the first lumen only; and a second plurality of apertures disposed in the catheter proximal to the second balloon and in communication with the second lumen only.

2. The catheter as defined in claim 1, wherein the proximal end further includes first and second inflation ports and a cardioplegia inlet port, the distal end further includes an outlet port, and the catheter further comprises third, fourth and fifth lumens, the third lumen provides fluid communication between the cardioplegia inlet port and the outlet port only, the fourth lumen provides fluid communication between the first inflation port and an interior of the first balloon only, and the fifth lumen provides fluid communication between the second inflation port and an interior of the second balloon only.

3. The catheter as defined in claim 1 further comprising a radioopaque marker adjacent the distal end.

4. The catheter as defined in claim 1 wherein the first balloon is longitudinally spaced apart from the second balloon so that when the first balloon is positioned in the patient's ascending aorta, the second balloon is located below the patient's renal arteries.

5. The catheter as defined in claim 1 wherein the catheter comprises:

an inner catheter that includes the first blood inlet port, the first inflation port, the cardioplegia inlet port, the outlet port, the first balloon, the first plurality of apertures, and first, third and fourth lumens; and an outer catheter that includes the second blood inlet port, the second inflation port, the second balloon, the second plurality of apertures, and second and fifth lumens.

6. The catheter system as defined in claim 5 wherein the inner catheter is disposed for sliding movement in the second lumen so that a longitudinal spacing between the first and second balloons may be adjusted.

7. The catheter system as defined in claim 5 further comprising a radioopaque marker adjacent the outlet port.

8. The catheter system as defined in claim 5 further comprising a radioopaque marker adjacent the second balloon.

9. The catheter system as defined in claim 5 wherein the first lumen has a first cross-sectional area and the second lumen has a second cross-sectional area, the first and second cross-sectional areas selected to control flow rates of blood through the first and second lumens when the first and second blood inlet ports are connected to a single pump.

10. The catheter system as defined in claim 5 wherein the outer catheter includes an endcap including a portion defining a bore, and the inner catheter extends through the bore in the endcap.

11. The catheter as defined in claim 1 wherein the first lumen has a first diameter and the second lumen has a second diameter, the first and second diameters selected to control flow rates of blood through the first and second lumens when the first and second blood inlet ports are connected to a single pump.

* * * * *